United States Patent [19]

Ehrenfreund et al.

[11] Patent Number: 4,589,911
[45] Date of Patent: May 20, 1986

[54] FUSED N-PHENYLSULFONYL-N-TRIAZINYLUREAS

[75] Inventors: Josef Ehrenfreund, Allschwil; Werner Föry, Basel, both of Switzerland

[73] Assignee: Ciba-Geigy Corporation, Ardsley, N.Y.

[21] Appl. No.: 606,076

[22] Filed: May 1, 1984

[30] Foreign Application Priority Data

May 11, 1983 [CH] Switzerland .................. 2592/83

[51] Int. Cl.$^4$ .................. C07D 411/12; A01N 43/68; A01N 43/70
[52] U.S. Cl. .................. 71/91; 71/93; 71/92; 544/212; 544/207; 544/209; 544/321; 544/324; 544/331; 544/49
[58] Field of Search .................. 71/93, 91; 544/212, 544/207, 209

[56] References Cited

FOREIGN PATENT DOCUMENTS

| 0044807 | 1/1982 | European Pat. Off. |
| 0044808 | 1/1982 | European Pat. Off. |
| 0051465 | 5/1982 | European Pat. Off. |
| 0079683 | 5/1983 | European Pat. Off. |
| 0107979 | 5/1984 | European Pat. Off. |

*Primary Examiner*—John M. Ford
*Attorney, Agent, or Firm*—Edward M. Roberts; Irving M. Fishman; Frederick H. Rabin

[57] ABSTRACT

Fused N-phenylsulfonyl-N'-triazinylurea of formula I

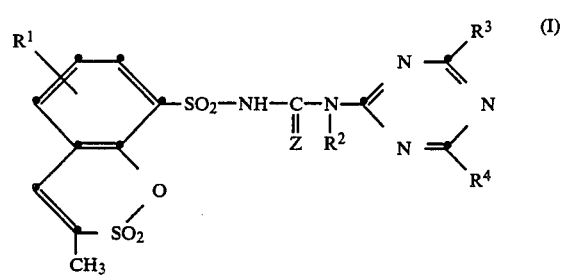

wherein

Z is oxygen or sulfur, $R^1$ is hydrogen, halogen, nitro, $C_1$-$C_4$alkyl, $C_1$-$C_4$haloalkyl, cyano, or a —X—$R^5$, —CO—X—$R^6$, —CO—$NR^7R^8$, —SO—$R^9$ or —$SO_2$—$R^{10}$ group, $R^2$ is hydrogen, $C_1$-$C_4$alkyl or $C_1$-$C_4$alkoxy, $R^3$ is $C_1$-$C_4$alkyl, $C_1$-$C_4$haloalkyl, $C_1$-$C_4$alkoxy, $C_1$-$C_4$haloalkoxy or $C_3$-$C_6$cycloalkyl, $R^4$ is hydrogen, halogen, $C_1$-$C_4$haloalkyl, $C_1$-$C_4$alkoxy, $C_1$-$C_4$haloalkoxy, $C_2$-$C_4$alkoxyalkoxy, $C_3$-$C_6$cycloalkyl or —$NR^{11}R^{12}$, $R^5$ is $C_3$-$C_5$alkynyl or $C_1$-$C_4$alkyl which is unsubstituted or substituted by halogen or $C_1$-$C_4$-alkoxy, or is $C_3$-$C_5$alkenyl, which is unsubstituted or is substituted by halogen or $C_1$-$C_4$-alkoxy, $R^6$ and $R^9$ are each independently $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, $R^7$ and $R^8$ are each independently hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, $R^{10}$ is $C_1$-$C_4$alkyl, $C_1$-$C_4$alkoxy, $C_1$-$C_4$haloalkoxy or —$NR^{13}R^{14}$, $R^{11}$ and $R^{12}$ are each independently hydrogen or $C_1$-$C_4$alkyl, $R^{13}$ and $R^{14}$ are each independently hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl, and X is oxygen or sulfur, or a salt thereof have good pre and post-emergence selective herbicidal and growth regulating properties.

14 Claims, No Drawings

FUSED N-PHENYLSULFONYL-N-TRIAZINYLUREAS

The present invention relates to novel fused N-phenylsulfonyl-N'-pyrimidinylureas and N-phenylsulfonyl-N'-triazinylureas having herbicidal and growth regulating properties, to the preparation thereof, to compositions containing them, and to the use of these novel compounds for controlling weeds, in particular selectively, in crops of useful plants, or for regulating and inhibiting plant growth. The invention further relates to novel fused phenylsulfonylisocyanates and phenylsulfonylthioisocyanates, phenylsulfonylcarbamates, phenylsulfonamides and phenylsulfonyl chlorides obtained as intermediates.

The fused N-phenylsulfonyl-N'-pyrimidinylureas and N-phenylsulfonyl-N'-triazinylureas, and the salts thereof, have the formula

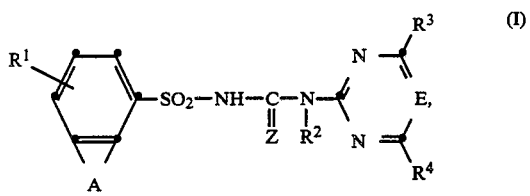

wherein
Z is oxygen or sulfur,
E is nitrogen or =CH—,
$R^1$ is hydrogen, halogen, nitro, $C_1$-$C_4$alkyl, $C_1$-$C_4$haloalkyl, cyano, or a —X—$R^5$, —CO—X—$R^6$, —CO—$NR^7R^8$, —SO—$R^9$ or —$SO_2$—$R^{10}$ group,
$R^2$ is hydrogen, $C_1$-$C_4$alkyl or $C_1$-$C_4$alkoxy,
$R^3$ is $C_1$-$C_4$alkyl, $C_1$-$C_4$haloalkyl, $C_1$-$C_4$alkoxy, $C_1$-$C_4$haloalkoxy or $C_3$-$C_6$cycloalkyl,
$R^4$ is hydrogen, halogen, $C_1$-$C_4$haloalkyl, $C_1$-$C_4$alkoxy, $C_1$-$C_4$haloalkoxy, $C_2$-$C_4$alkoxyalkoxy, $C_3$-$C_6$cycloalkyl or —$NR^{11}R^{12}$,
$R^5$ is $C_3$-$C_5$alkynyl or $C_1$-$C_4$alkyl which is unsubstituted or substituted by halogen or $C_1$-$C_4$-alkoxy, or is $C_3$-$C_5$alkenyl, which is unsubstituted or is substituted by halogen or $C_1$-$C_4$-alkoxy,
$R^6$ and $R^9$ are each independently $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl,
$R^7$ and $R^8$ are each independently hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl,
$R^{10}$ is $C_1$-$C_4$alkyl, $C_1$-$C_4$alkoxy, $C_1$-$C_4$haloalkoxy or —$NR^{13}R^{14}$,
$R^{11}$ and $R^{12}$ are each independently hydrogen or $C_1$-$C_4$alkyl,
$R^{13}$ and $R^{14}$ are each independently hydrogen, $C_1$-$C_4$alkyl, $C_1$-$C_4$haloalkyl, $C_2$-$C_4$alkoxyalkyl, $C_3$-$C_5$alkenyl, $C_3$-$C_5$alkynyl, phenyl or benzyl,
X is oxygen or sulfur, and
A is an unsubstituted or substituted unsaturated bridge of 4 atoms, of the formula —CH=CH—Y—, wherein Y is a bridge member of 2 atoms which is selected from the series consisting of —NH—CO—, —NH—$SO_2$—, —S—CO—, —S—$SO_2$—, —O—CO— or —O—$SO_2$—.

Ureas, triazines and pyrimidines with herbicidal properties are generally known in the art. Sulfonylureas with herbicidal and plant growth-regulating action have recently been described e.g. in European patent applications 44 807, 44 808 and 51 465.

In the above definitions, alkyl denotes straight-chain or branched alkyl, e.g. methyl, ethyl, n-propyl, isopropyl, or the four butyl isomers.

Alkoxy denotes methoxy, ethoxy, n-propoxy, isopropoxy, the four butoxy isomers, with methoxy, ethoxy or isopropoxy being preferred.

Alkylthio is e.g. methylthio, ethylthio, n-propylthio, isopropylthio, or n-butylthio, with methylthio and ethylthio being preferred.

Alkylsulfinyl is e.g. methylsulfinyl, ethylsulfinyl, n-propylsufinyl and n-butylsulfinyl, with methylsulfinyl and ethylsulfinyl being preferred.

Alkylsulfonyl is e.g. methylsulfonyl, ethylsulfonyl or n-propylsulfinyl, with methylsulfonyl and ethylsulfonyl being preferred.

Halogen in the above definitions, as well as moiety of haloalkyl, and haloalkoxy is fluorine, chlorine and bromine, with fluorine and chlorine being preferred.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation. The tetraethylammonium cation, the trimethylethylammonium cation, and also the ammonium cation.

Examples of suitable substituents of the bridge A are: halogen, cyano, $C_1$-$C_4$ alkyl, $C_1$-$C_4$ haloalkyl, $C_1$-$C_4$ alkoxy, $C_1$-$C_4$ alkylcarbonyl, $C_1$-$C_4$ alkoxycarbonyl, $C_1$-$C_4$ alkylthiocarbonyl, carbamoyl, $C_1$-$C_4$ alkylaminocarbonyl, di($C_1$-$C_4$)alkylaminocarbonyl, $C_1$-$C_4$-alkylsulfonyl, $C_3$-$C_5$ alkenyl or $C_3$-$C_5$ alkynyl.

Condensed heterocyclic unsaturated ring systems, in which the sulfur and carbon atoms contained as chain members may also be present in oxidised form, are formed by the phenyl ring and the fused bridge A containing 4 atoms. Accordingly, the present invention also encompasses those heterocyclic systems which contain lactone, thiolactone, lactam, sultone or sultam functions.

Typical representatives of the basic types of condensed heterocyclic systems which are formed by the sulfonyl-substituted phenyl ring and the fused bridge A are: 2H-1-benzopyrane (chromene), 2H-1-benzothiopyrane, 2H-1-benzopyranone (coumarin), 2H-1-benzothiopyrone, 1H-2-benzopyranone, 1H-2-benzothiopyranone, 1-isoquinolone, 2-quinolone, 1-quinolone, 1,2-benzoxathiine-S,S-dioxide and 1H-2,1-benzothiazine-S,S-dioxide.

Preferred compounds of the formula I are those in which either
(a) the substituents of the bridge A are halogen or $C_1$–$C_4$ alkyl, or
(b) Z is oxygen, or
(c) $R^1$ is hydrogen or halogen, or
(d) $R^2$ is hydrogen, or
(e) $R^3$ and $R^4$, independently of each other, are $C_1$–$C_4$ alkyl, $C_1$–$C_4$ alkoxy, di($C_1$–$C_4$)alkylamino, $C_1$–$C_4$ haloalkoxy or halogen, and together contain not more than 4 carbon atoms.

Further preferred subgroups comprise those compounds of formula I in which Z is oxygen, $R^1$ is hydrogen or halogen, $R^2$ is hydrogen, and each of $R^3$ and $R^4$ independently of the other is $C_1$–$C_4$ alkyl, $C_1$–$C_4$ alkoxy, di($C_1$–$C_4$)alkylamino, $C_1$–$C_4$ haloalkoxy or halogen, and together contain not more than 4 carbon atoms.

A particularly preferred group of compounds of formula I comprises those compounds in which Z is oxygen, $R^1$ is hydrogen, halogen or $C_1$–$C_4$ alkoxycarbonyl, $R^2$ is hydrogen, each of $R^3$ and $R^4$ independently of the other is $C_1$–$C_4$ alkyl, $C_1$–$C_4$ alkoxy, di($C_1$–$C_4$)alkylamino, $C_1$–$C_4$ haloalkoxy or halogen, and together contain not more than 4 carbon atoms, and the bridge A is unsubstituted or substituted by halogen or $C_1$–$C_4$ alkyl.

Preferred individual compounds are:
N-(2-methyl-1-isoquinolon-5-ylsulfonyl)-N'-(4-methoxy-6-methyl-1,3,5-triazin-2-yl)urea,
N-(3-methyl-2,2-dioxo-1,2-benzoxathiin-8-ylsulfonyl)-N'-(4-difluoromethyl-6-methylpyrimidin-2-yl)urea,
N-(6-bromo-3-methyl-2,2-dioxo-1,2-benzoxathiin-8-ylsulfonyl)-N'-(4-methoxy-6-methyl-1,3,5-triazin-2-yl)urea,
N-(3-methyl-2,2-dioxo-1,2-benzoxathiin-8-ylsulfonyl)-N'-(4-methoxy-6-methyl-1,3,5-triazin-2-yl)urea.

The preparation of the compounds of formula I is generally carried out by the following methods.

A first process for the preparation of the compounds of formula I comprises reacting a fused phenylsulfonamide of the formula II

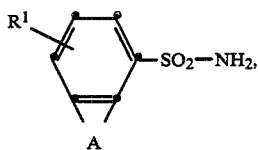

wherein $R^1$ and A are as defined for formula I, with an N-pyrimidinylcarbamate or N-triazinylcarbamate of the formula III

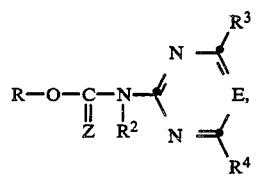

wherein E, $R^2$, $R^3$, $R^4$ and Z are as defined for formula I and R is phenyl, alkyl or substituted phenyl, in the presence of a base.

A second process for obtaining the compounds of formula I comprises reacting a fused phenylsul-fonylisocyanate or phenylsulfonylisothiocyanate of the formula IV

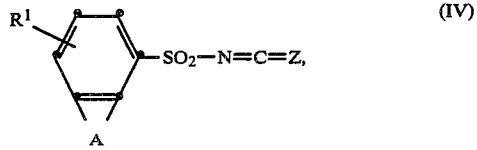

wherein A, $R^1$ and Z are as defined for formula I, with an aminopyridine or aminotriazine of the formula V

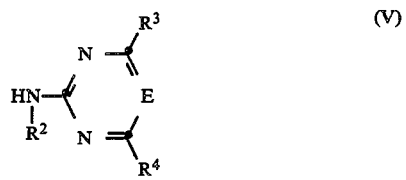

wherein E, $R^2$, $R^3$ and $R^4$ are as defined for formula I, in the presence of a base.

Finally, the compounds of formula I may also be obtained by reacting a fused N-phenylsulfonylcarbamate of the formula VI

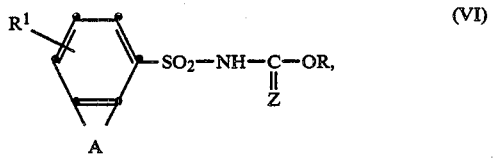

wherein A, $R^1$ and Z are as defined for formula I and R is phenyl, alkyl or substituted phenyl, with an aminopyrimidine or aminotriazine of the formula V above.

If desired, the ureas of formula I so obtained can be converted into addition salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

It is convenient to carry out these reactions for obtaining compounds of formula I in aprotic, inert organic solvents.

Examples of such solvents are: benzene, toluene, xylene or cyclohexane; chlorinated hydrocarbons such as methylene chloride, chloroform, carbon tetrachloride, or chlorobenzene; ethers such as diethyl ether, ethylene glycol dimethyl ether, diethylene glycol dimethyl ether, tetrahydrofuran or dioxane; nitriles such as acetonitrile or propionitrile; amides such as dimethylformamide, diethylformamide or N-methylpyrrolidinone.

The reaction temperatures are preferably in the range from $-20°$ to $+120°$ C. The coupling reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst. Prefered bases are tertiary amines such as trimethylamine, triethylamine, quinuclidine, 1,4-diazabicyclo[2,2,2]octane, 1,5-diazabicyclo[4,3,0]- non-5-ene or 1,8-diazabicyclo[5,4,0]undec-7-ene. However, the based employed may also be inorganic bases, e.g. hydrides such as sodium hydride or calcium hydride, hydroxides such as sodium hydroxide or potassium hydroxide, carbonates such as sodium or potassium carbonate, or bicarbonates such as potassium or sodium bicarbonate.

The final products of formula I can be isolated by concentrating the reaction mixture and/or removing the solvent by evaporation, and by recrystallisation or by triturating the solid residue in a solvent in which it is poorly soluble, such as an ether, an aromatic hydrocarbon or a chlorinated hydrocarbon.

The intermediates of forulae II, IV and VI are novel and have been specially developed for the synthesis of compounds of the formula I. Accordingly, they constitute an object of the present invention.

The novel intermediates of the formula II can be prepared by different methods. For example, the compounds of formula II are obtained by diazotising anilines of formula VII

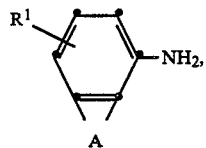

wherein $R^1$ and A are as defined for formula I, and replacing the diazo group with sulfur dioxide, in the presence of a catalyst such as copper chloride, in hydrochloric acid or acetic acid, and reacting the resultant phenylsulfonyl chloride of the formula X

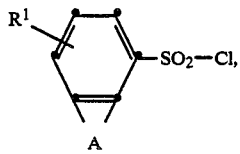

wherein A and $R^1$ are as defined for formula I, with ammonium hydroxide solution. The corresponding aniline derivatives employed as starting materials are known or they can be prepared by known methods.

Likewise, the compounds of formula II can be obtained by converting a phenylsulfonic acid of the formula VIII

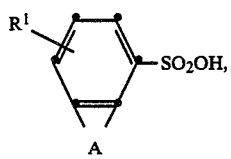

wherein $R^1$ and A are as defined for formula I, by treatment with a chlorinating agent such as $PCl_5$, $POCl_3$, $COCl_2$ or $SOCl_2$, to the corresponding phenylsulfonyl chloride of the formula X, and reacting this chloride with ammonium hydroxide solution.

The compounds of formula II can also be obtained by converting a benzyl thioether of the formula IX

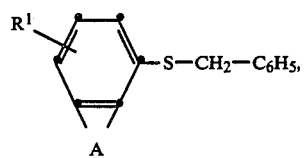

wherein $R^1$ and A are as defined for formula I, by treatment with chlorine, and reacting the resultant phenylsulfonyl chloride of the formula X with ammonium hydroxide solution.

The phenylsulfonyl isocyanates of the formula IV, which are also novel, can be obtained by phosgenating the sulfonamides of the formula II, in the presence of butylisocyanate, in a chlorinated hydrocarbon as solvent, at reflux temperature. Similar reactions are described in "Neuere Methoden der präparativen organischen Chemie", Band. VI, 211-229, Verlag Chemie, Weinheim, 1970.

The isothiocyanates of the formula IV are obtained by treating the sulfonamides of formula II with carbon disulfide and potassium hydroxide and subsequently phosgenating the dipotassium salt. Such processes are described in Arch. Pharm. 299, 174 (1966).

The N-phenylsulfonylcarbamates of the formula VI are obtained by reacting the sulfonamides of the formula II with diphenyl carbonate in the presence of a base. Similar processes are described in Japanese patent specification 61 169.

The fused phenylsulfonyl chlorides of the formula X, which are also novel, have likewise been specially developed for the synthesis of the compounds of formula I. Accordingly, they also constitute a further object of this invention.

The starting aminopyrimidines and aminotriazines of the formula V, as well as corresponding phenylcarbamates of the formula III, have either long been known or are described in European patent application 70 804, or they can be prepared by known methods from compounds disclosed therein.

The final products can be isolated by concentrating the reaction mixture and/or evaporating off the solvent, and purified by recrystallising or triturating the solid residue in solvents in which they are not readily soluble, e.g. in an ether, an aromatic hydrocarbon or a chlorinated hydrocarbon.

The compounds of formula I are stable compounds, and no protective measures are required for handling them.

When used at low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the nvel compounds of the formula I are effective even when used at very low rates of application.

The compounds of formula I have in addition pronounced growth-regulating, especially growth-inhibiting, properties. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whilst vegetative growth is inhibited.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contains a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g.

stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I-III, Chemical Publishing Co., N.Y., 1980-81.

The pesticidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples.

PREPARATORY EXAMPLES

Example H1

N-(6-Bromo-2,2-dioxo-1,2-benzoxathiin-8-ylsulfonyl)-N'-(4,6-dimethoxypyrimidin-2-yl)urea (a) 6-Bromo-3,4-dihydro-4-hydroxy-2,2-dioxo-1,2-benzoxathiine 24.2 g of salicylaldehyde are dissolved in 100 ml of absolute pyridine and 17 ml of methylsulfonyl chloride are added dropwise at 0° C. to this solution. After the reaction mixture has been stirred for 5 hours at 20°-25° C. it is poured into a mixture of ice and 10% hydrochloric acid. This mixture is extracted with ether and the organic phases are dried over sodium sulfate and concentrated, affording 30 g of 5-bromo-2-methylsulfonyloxy benzaldehyde. This intermediate is dissolved in 100 ml of methylene chloride and 16 ml of 1,8-diazabicyclo[5.4.0]undec-7-ene are added dropwise to the solution at 0° C. The mixture is then stirred for 30 minutes and poured into a mixture of ice and 10% hydrochloric acid. After extraction with ether, the organic phase is dried and concentrated, affording 23.0 g of 6-bromo-3,4-dihydro-4-hydroxy-2,2-dioxo-1,2-benzoxathiine.

(b) 6-Bromo-2,2-dioxo-1,2-benzoxathiine

The 23.0 g of 6-bromo-3,4-dihydro-4-hydroxy-2,2-dioxo-1,2-benzoxathiine obtained in (a) are dissolved in 50 ml of pyridine without further purification. The solution is then cooled to 0° C. and 16.0 g of phosphoroxy trichloride is then added dropwise. After the mixture has been stirred for 3 hours at 20°-25° C., it is cautiously poured into ice-water and the the product precipitates. The precipitate is isolated and recrystallised from ethanol, affording 17.5 g (82% of theory) of 6-bromo-2,2-dioxo-1,2-benzoxathiine of m.p. 140°-141.5° C.

(c) 6-Bromo-8-chlorosulfonyl-2,2-dioxo-1,2-benzoxathiine 6.0 g of 6-bromo-2,2-dioxo-1,2-benzoxathiine and 22.0 g of chlorosulfonic acid are heated for 1 hour to 60° C. The mixture is then poured into ice-water. The precipitated 6-bromo-8-chlorosulfonyl-2,2-dioxo-1,2-benzoxathiine is isolated, washed with water and dried.

(d) 6-Bromo-8-sulfamoyl-2,2-dioxo-1,2-benzoxathiine

The crystalline product obtained in (c) is dissolved in as small an amount of tetrahydrofuran as possible and the solution is added dropwise to 20 ml of 25% aqueous ammonia solution. After the reaction mixture has been stirred for 30 minutes it is poured into a mixture of ice and 10% hydrochloric acid. Extraction with ether yields 0.3 g of 6-bromo-8-sulfamoyl-2,2-dioxo-1,2-benzoxathiine of m.p. 224°-228° C. (decomposition with black colouration).

(e) N-(6-bromo-2,2-dioxo-1,2-benzoxathiin-8-ylsulfonyl)-N'-(4,6-dimethoxypyrimidin-2-yl)urea 0.3 g of 6-bromo-8-sulfamoyl-2,2-dioxo-1,2-benzoxathiine are dissolved in 10 ml of acetonitrile. To this solution are added 0.25 g of N-(4,6-dimethoxypyrimidin-2-yl)phenylcarbamate and 0.15 g of 1,8-diazabicyclo[5.4.0]undec-7-ene and the mixture is stirred for 2 hours at 20°-25° C. The mixture is then acidified with 5% hydrochloric acid and diluted with water. The precipitated oil is extracted with ethyl acetate and the combined organic phases are washed with water, dried and concentrated. The oily residue is crystallised from ether, affording 0.3 g of N-(6-bromo-2,2-dioxo-1,2-benzoxathiin-8-ylsulfonyl)-N'-(4,6-dimethoxypyrimidin-2-yl)urea of m.p. 204°-209° C. (decompos.).

Example H2

3-Methyl-2,2-dioxo-1,2-benzoxathiin-8-ylsulfonylisocyanate (a) N-(3-Methyl-2,2-dioxo-1,2-benzoxathiin-8-ylsulfonyl)-N'-methylurea 1.15 g of methyl isocyanate are added dropwise at 0° C. to a solution of 5.5 g of 3-methyl-8-sulfamoyl-2,2-dioxo-1,2-benzoxathiine and 3.2 g of 1,8-diazabicyclo[5.4.0]undec-7-ene. The reaction mixture is stirred for 2 hours at 20°-25° C., then diluted with water, neutralised with 5% sodium carbonate solution and filtered. The filtrate is acidified and 5.4 g of N-(3-methyl-2,2-dioxo-1,2-benzoxathiin-8-yl-sulfonyl)-N'-methylurea precipitate. This precipitate is isolated and dried.

(b) 3-Methyl-2,2-dioxo-1,2-benzoxathiin-8-ylsulfonylisocyanate 5.0 g of N-(3-methyl-2,2-dioxo-1,2-benzoxathiin-8-ylsulfonyl)-N'-methylurea are dispersed in 150 ml of absolute chlorobenzene and the dispersion is saturated with phosgene at 130° C. A clear solution forms during this addition. The solvent is subsequently distilled off in vacuo with the exclusion of moisture. The 3-methyl-2,2-dioxo-1,2-benzoxathiin-8-ylsulfonylisocyanate obtained as oily residue can be used without further purification for the preparation of the pyrimidinylureas and triazinylureas of the formula I.

The intermediates and final products listed in the following tables are obtained in corresponding manner.

TABLE 1

Q—SO$_2$—NH$_2$

| Compound | Q | Abbreviation for Q | Physical data |
|---|---|---|---|
| 1.1 | (structure) | Q 1 | m.p. 224–246° C. |
| 1.2 | (structure) | Q 2 | m.p. 253–255° C. |
| 1.3 | (structure) | Q 3 | m.p. 205–206° C. |
| 1.4 | (structure) | Q 4 | |

TABLE 2

Q—SO$_2$—Cl

| Compound | Q | Physical data |
|---|---|---|
| 2.1 | Q1 | brown oil |
| 2.2 | Q2 | |
| 2.3 | Q3 | |
| 2.4 | Q4 | |

TABLE 3

Q—SO$_2$—N=C=O

| Compound | Q | Physical data |
|---|---|---|
| 3.1 | Q1 | oil |
| 3.2 | Q2 | oil |
| 3.3 | Q3 | oil |
| 3.4 | Q4 | oil |

TABLE 4

Q—SO$_2$—NH—CO—T

| Compound | Q | T | Physical data |
|---|---|---|---|
| 4.1 | Q1 | OC$_6$H$_5$ | |
| 4.2 | Q2 | OC$_6$H$_5$ | |
| 4.3 | Q3 | OC$_6$H$_5$ | |
| 4.4 | Q4 | OC$_6$H$_5$ | |
| 4.5 | Q1 | OCH$_3$ | |
| 4.6 | Q2 | OCH$_3$ | |
| 4.7 | Q3 | OCH$_3$ | |
| 4.8 | Q4 | OCH$_3$ | |
| 4.9 | Q1 | OC$_2$H$_5$ | |
| 4.10 | Q2 | OC$_2$H$_5$ | |
| 4.11 | Q3 | OC$_2$H$_5$ | |
| 4.12 | Q4 | OC$_2$H$_5$ | |
| 4.13 | Q1 | —NHCH$_3$ | |
| 4.14 | Q2 | —NHCH$_3$ | |
| 4.15 | Q3 | —NHCH$_3$ | |
| 4.16 | Q4 | —NHCH$_3$ | |

TABLE 5

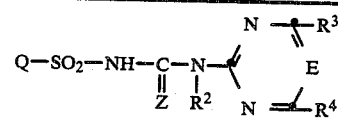

Q has the meanings indicated in Table 1 for the fused phenyl ring

| Compound | Q | R$^2$ | R$^3$ | R$^4$ | Z | E | m.p. [°C.] |
|---|---|---|---|---|---|---|---|
| 5.1 | Q 1 | H | CH$_3$ | OCH$_3$ | O | N | 258–262 |
| 5.2 | Q 1 | H | OCH$_3$ | OCH$_3$ | O | N | |
| 5.3 | Q 1 | H | OCH$_3$ | —N(CH$_3$)$_2$ | O | N | |
| 5.4 | Q 1 | H | OCH$_3$ | —OCH$_2$—CF$_3$ | O | N | |
| 5.5 | Q 1 | H | CH$_3$ | CH$_3$ | O | CH | |
| 5.6 | Q 1 | H | OCH$_3$ | CH$_3$ | O | CH | 260 (decompos.) |
| 5.7 | Q 1 | H | OCH$_3$ | OCH$_3$ | O | CH | |
| 5.8 | Q 1 | H | CH$_3$ | OCHF$_2$ | O | CH | |
| 5.9 | Q 2 | H | OCH$_3$ | CH$_3$ | O | N | 196–198 |
| 5.10 | Q 2 | H | OCH$_3$ | OCH$_3$ | O | N | |
| 5.11 | Q 2 | H | OCH$_3$ | —N(CH$_3$)$_2$ | O | N | |
| 5.12 | Q 2 | H | OCH$_3$ | —OCH$_2$—CF$_3$ | O | N | |
| 5.13 | Q 2 | H | CH$_3$ | C$_2$H$_5$ | O | N | |
| 5.14 | Q 2 | H | CH$_3$ | CH$_3$ | O | CH | |
| 5.15 | Q 2 | H | CH$_3$ | OCH$_3$ | O | CH | |
| 5.16 | Q 2 | H | OCH$_3$ | OCH$_3$ | O | CH | |
| 5.17 | Q 2 | H | CH$_3$ | OCHF$_2$ | O | CH | |
| 5.18 | Q 3 | H | CH$_3$ | OCH$_3$ | O | N | 203–205 |
| 5.19 | Q 3 | H | OCH$_3$ | OCH$_3$ | O | N | |
| 5.20 | Q 3 | H | OCH$_3$ | —N(CH$_3$)$_2$ | O | N | |
| 5.21 | Q 3 | H | CH$_3$ | C$_2$H$_5$ | O | N | |
| 5.22 | Q 3 | H | OCH$_3$ | C$_2$H$_5$ | O | N | |
| 5.23 | Q 3 | H | OC$_2$H$_5$ | C$_2$H$_5$ | O | N | |
| 5.24 | Q 3 | H | OCH$_3$ | —OCH$_2$—CF$_3$ | O | N | |
| 5.25 | Q 3 | H | CH$_3$ | —OCH$_2$—CF$_3$ | O | N | |
| 5.26 | Q 3 | H | OCH$_3$ | OC$_3$H$_7$—i | O | N | |
| 5.27 | Q 3 | H | SCH$_3$ | OCH$_3$ | O | N | |
| 5.28 | Q 3 | H | OCH$_3$ | —NHCH$_3$ | O | N | |
| 5.29 | Q 3 | H | CH$_3$ | CH$_3$ | O | N | |
| 5.30 | Q 3 | H | CH$_3$ | CH$_3$ | O | CH | |
| 5.31 | Q 3 | H | OCH$_3$ | CH$_3$ | O | CH | |
| 5.32 | Q 3 | H | OCH$_3$ | OCH$_3$ | O | CH | |
| 5.33 | Q 3 | H | CH$_3$ | —OCH$_2$—CF$_3$ | O | CH | |
| 5.34 | Q 3 | H | CH$_3$ | OC$_2$H$_5$ | O | CH | |
| 5.35 | Q 3 | H | OCH$_3$ | Cl | O | CH | |
| 5.36 | Q 3 | H | OCH$_3$ | SCHF$_2$ | O | CH | |
| 5.37 | Q 3 | H | OCH$_3$ | —N(CH$_3$)$_2$ | O | CH | |
| 5.38 | Q 3 | H | OCH$_3$ | —NHCH$_3$ | O | CH | |
| 5.39 | Q 3 | H | OCH$_3$ | CH$_2$F | O | CH | |
| 5.40 | Q 3 | H | OCH$_3$ | CF$_3$ | O | CH | |
| 5.41 | Q 3 | H | OCH$_3$ | SCH$_3$ | O | CH | |
| 5.42 | Q 3 | H | OCH$_3$ | OCH$_2$—CF$_3$ | O | CH | |
| 5.43 | Q 3 | H | OCH$_3$ | —CH$_2$—OCH$_3$ | O | CH | |
| 5.44 | Q 3 | H | OCH$_3$ | —CH$_2$—OC$_2$H$_5$ | O | CH | |
| 5.45 | Q 4 | H | OCH$_3$ | OCH$_3$ | O | CH | 204–209 |
| 5.46 | Q 3 | H | CH$_3$ | OCHF$_2$ | O | CH | 189– |

TABLE 5-continued

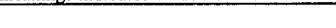

Q has the meanings indicated in Table 1 for the fused phenyl ring

| Compound | Q | R² | R³ | R⁴ | Z | E | m.p. [°C.] |
|---|---|---|---|---|---|---|---|
| | | | | | | | 191 |
| 5.47 | Q 3 | H | OCHF₂ | OCHF₂ | O | CH | |
| 5.48 | Q 3 | H | OCH₃ | cyclopropyl | O | N | |
| 5.49 | Q 3 | H | OCH₃ | cyclopropyl | O | CH | |
| 5.50 | Q 3 | H | OC₂H₅ | cyclopropyl | O | N | |
| 5.51 | Q 3 | H | OC₂H₅ | cyclopropyl | O | CH | |

FORMULATION EXAMPLES

Example F1

Formulation Examples for compounds of formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula | 3% |
| polyethylene glycol 200 | 2% |
| kaolin | 94% |

The finely ground active ingredient is uniformly applied, in a mixer, to the kaolin moistened with polyethyene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrated from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

Example B1

Preemergence herbicidal action

Plastic pots are filled with expanded vermiculite (density: 0.135 g/cm³, water-absorbing capacity: 0.565 l/l). After the nonadsorptive vermiculite has been saturated with an aqueous emulsion in deionised water which contains the test compound in a concentration of 70.8 ppm, seeds of the following plants are sown on the surface: *Nasturtium officinalis*, *Agrostis tenuis*, *Stellaria media* and *Digitaria sanguinalis*. The pots are then kept in a climatic chamber at 20° C., an illumination of about 20 lux and a relative humidity of 70%. During the germinating phase of 4 to 6 days, the pots are covered with lightpermeable material and watered with deionised water to increase the local humidity. After the 5th day, 0.5% of a commercial liquid fertilizer (Greenzit ®, ex Ciba-Geigy) is added to the water. The test is evaluated 12 days after sowing and the action on the plants is assessed according to the following rating:
1: plants have not emerged or are totally withered 2-3: very pronounced action
4-6: medium action
7-8: weak action
9: no action (as untreated controls).

PREEMERGENCE ACTION

Concentration of the test compound emulsion: 70.8 ppm

| Compound | Test plant | | | |
|---|---|---|---|---|
| | Nasturtium | Stellaria | Agrostis | Digitaria |
| 5.9 | 1 | 1 | 1 | 2 |
| 5.18 | 1 | 1 | 1 | 1 |
| 5.46 | 2 | 2 | 2 | 2 |

Example B2

Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated at 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

Example B3

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The rate of application corresponds to 100 g a.i. per hectare. Evaluation is made about 5 weeks after application. Compared with untreated controls, the compounds of the formula I markedly increase the number and weight of the harvested siliques on the leading shoot.

Example B4

Growth inhibition of cereals

Summar barley (Hordeum vulgare) and summer rye (Secale) are sown in sterilised soil in plastic beakers in a greenhouse and watered as required. The cereal shoots are treated about 21 days after sowing with an aqueous spray mixture of a compound of the formula I. The concetration corresponds to 100 g of active ingredient per hectare. Evaluation of the growth of the cereals is made 21 days after application. A comparison with untreated controls shows that the growth of cereal plants treated with compounds of the formula I is significantly reduced (60-90% of the controls) and that the diameter of the stalks has in some cases increased.

Example B5

Growth inhibition of grasses

Seeds of the grasses Lolium perenne, Poa pratensis, Festuca ovina, Dactylis glomerate and Cynodon dactylon are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of the formula I. The concentration of test compound corresponds to a rate of application of up to 100 g a.i. per hectare. The growth of the grasses is evaluated 21 days after application. The compounds of formula I effect a reduction in new growth in the range of 10-30% in comparison with untreated controls.

What is claimed is:

1. A fused N-phenylsulfonyl-N'-triazylurea of the formula I

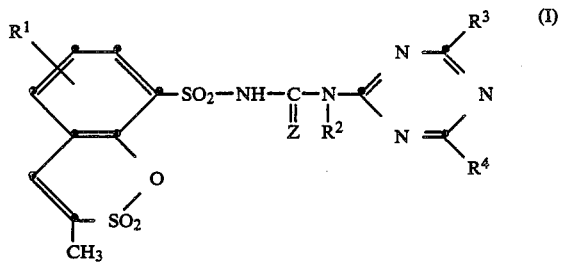

wherein

Z is oxygen or sulfur, $R^1$ is hydrogen, halogen, nitro, $C_1-C_4$alkyl, $C_1-C_4$haloalkyl, cyano, or a $-X-R^5$, $-CO-X-R^6$, $-CO-NR^7R^8$, $-SO-R^9$ or $-SO_2-R^{10}$ group, $R^2$ is hydrogen, $C_1-C_4$alkyl or $C_1-C_4$alkoxy, $R^3$ is $C_1-C_4$alkyl, $C_1-C_4$haloalkyl, $C_1-C_4$alkoxy, $C_1-C_4$haloalkoxy or $C_3-C_6$cycloalkyl, $R^4$ is hydrogen, halogen, $C_1-C_4$haloalkyl, $C_1-C_4$alkoxy, $C_1-C_4$haloalkoxy, $C_2-C_4$alkoxyalkoxy, $C_3-C_6$cycloalkyl or $-NR^{11}R^{12}$, $R^5$ is $C_3-C_5$alkynyl or $C_1-C_4$alkyl which is unsubstituted or substituted by halogen or $C_1-C_4$-alkoxy, or is $C_3-C_5$alkenyl, which is unsubstituted or is substituted by halogen or $C_1-C_4$-alkoxy, $R^6$ and $R^9$ are each independently $C_1-C_4$alkyl, $C_1-C_4$haloalkyl, $C_2-C_4$alkoxyalkyl, $C_3-C_5$alkenyl, $C_3-C_5$alkynyl, phenyl or benzyl, $R^7$ and $R^8$ are each independently hydrogen, $C_1-C_4$alkyl, $C_1-C_4$haloalkyl, $C_2-C_4$alkoxyalkyl, $C_3-C_5$alkenyl, $C_3-C_5$alkynyl, phenyl or benzyl, $R^{10}$ is $C_1-C_4$alkyl, $C_1-C_4$alkoxy, $C_1-C_4$haloalkoxy or $-NR^{13}R^{14}$, $R^{11}$ and $R^{12}$ are each independently hydrogen or $C_1-C_4$alkyl, $R^{13}$ and $R^{14}$ are each independently hydrogen, $C_1-C_4$alkyl, $C_1-C_4$haloalkyl, $C_2-C_4$alkoxyalkyl, $C_3-C_5$alkenyl, $C_3-C_5$alkynyl, phenyl or benzyl, and X is oxygen or sulfur, or a salt thereof.

2. A compound according to claim 1, wherein Z is oxygen.

3. A compound according to claim 1, wherein $R^1$ is hydrogen or halogen.

4. A compound according to claim 1, wherein $R^2$ is hydrogen.

5. A compound according to claim 1, wherein each of $R^3$ and $R^4$ independently of the other is $C_1$–$C_4$ alkyl, $C_1$–$C_4$ alkoxy, di($C_1$–$C_4$)-alkylamino, $C_1$–$C_4$ haloalkoxy or halogen, and together contain not more than 4 carbon atoms.

6. A compound according to claim 1, wherein Z is oxygen, $R^1$ is hydrogen or halogen, $R^2$ is hydrogen, each of $R^3$ and $R^4$ independently of the other is $C_1$–$C_4$ alkyl, $C_1$–$C_4$ alkoxy, di($C_1$–$C_4$) alkylamino, $C_1$–$C_4$ haloalkoxy or halogen, and together contain not more than 4 carbon atoms.

7. N-(3-Methyl-2,2-dioxo-1,2-benzoxathiin-8-ylsulfonyl)-N'-(4-methoxy-6-methyl-1,3,5-triazin-2-yl)urea according to claim 1.

8. N-(6-Bromo-3-methyl-2,2-dioxo-1,2-benzoxathiin-8-ylsulfonyl)-N'-(4-methoxy-6-methyl-1,3,5-triazin-2-yl)urea according to claim 1.

9. N-(3-Methyl-2,2-dioxo-1,2-benzoxathiin-8-ylsulfonyl)-N'-(4,6-dimethoxy-1,3,5-triazin-2-yl)urea according to claim 1.

10. A herbicidal and plant growth inhibiting composition which contains at least one fused N-phenylsulfonyl-N'-triazinylurea of the formula I as claimed in claim 1, together with carriers and/or other adjuvants.

11. A method of controlling undesired plant growth, which comprises applying an effective amount of a compound of the formula I according to claim 1 to the plant or the locus thereof.

12. A method of inhibiting plant growth, which comprises applying an effective amount of a compound of the formula I according to claim 1 to the plant or the locus thereof.

13. A method of influencing plant growth for increasing yield, which comprises applying an effective amount of a compound of the formula I according to claim 1 to the plant or the locus thereof.

14. A method according to claim 12 of selectively controlling weeds pre- or postemergence in crops of useful plants, which method comprises applying an effective amount of a compound of the formula I to the plant or the locus thereof.

* * * * *